United States Patent [19]

Devlin

[11] Patent Number: 4,560,401

[45] Date of Patent: Dec. 24, 1985

[54] METHOD FOR STERILIZING MALE PARTS OF PLANTS

[75] Inventor: Barry R. J. Devlin, Sittingbourne, England

[73] Assignee: Shell Oil Company, Houston, Tex.

[21] Appl. No.: 523,226

[22] Filed: Aug. 15, 1983

Related U.S. Application Data

[63] Continuation-in-part of Ser. No. 395,401, Jul. 6, 1982, abandoned, and a continuation of Ser. No. 289,552, Aug. 3, 1981, abandoned, and a continuation of Ser. No. 201,107, Oct. 28, 1980, abandoned, and a continuation-in-part of Ser. No. 395,526, Jul. 6, 1982, abandoned.

[30] Foreign Application Priority Data

Nov. 16, 1979 [GB] United Kingdom ................. 7939781

[51] Int. Cl.$^4$ ............................................ A01N 43/00
[52] U.S. Cl. ...................................................... 71/88
[58] Field of Search ............................................. 71/88

[56] References Cited

U.S. PATENT DOCUMENTS 4,047,930 9/1977 Kerr ........................................ 71/76

OTHER PUBLICATIONS

Britikov et al., "Effect of Proline, etc.," (1966), Fisiol. Rast. 13, No. 6, pp. 1-18 (Eng. Trans).
Isono et al., "Studies on Polyoxins, etc.," (1969), JACS 91, pp. 7490-7505, (1969).
Anderson, Jr. et al., "The Synthesis of, etc.," (1972), J. Org. Chem., vol. 37, No. 24, pp. 3953-3955, (1972).

*Primary Examiner*—Glennon H. Hollrah
*Assistant Examiner*—Andrew Duff Meikle

[57] ABSTRACT

3-Substituted-2-carboxyazetidines, their esters and salts are used to sterilize male parts in plants.

7 Claims, No Drawings

METHOD FOR STERILIZING MALE PARTS OF PLANTS

This application is a continuation-in-part of application Ser. No. 395,401, filed July 6, 1982, abandoned, a continuation of application Ser. No. 289,552, filed on Aug. 3, 1981, abandoned, a continuation of application Ser. No. 201,107, filed on Oct. 28, 1980, abandoned. This application also is a continuation-in-part of application Ser. No. 395,526, filed July 6, 1982, abandoned, a continuation-in-part of application Ser. No. 289,552.

BACKGROUND OF THE INVENTION

To obtain $F_1$ hybrid seeds, which have many advantages over non-hybrid seeds, seed breeders cross-pollinate carefully selected parent plants. In the case of plants, for example small grain cereal plants, which have hermaphroditic flowers and normally self-pollinate, this is achieved by removing the male anthers from each of the flowers by hand, an operation which is extremely time consuming and requires highly-skilled workers. Much research is being carried out into treatments with chemicals by which this same result can be achieved without the necessity for such hand-operations.

DESCRIPTION OF THE INVENTION

It has now been found that certain 3-substituted-2-carboxyazetidine compounds sterilize the male parts of plants, by way of rendering the pollen grains nonfunctional—i.e., sterile. The present invention thus provides a method of sterilizing the male parts of a plant, which comprises applying to a plant an effective amount of a 3-substituted-2-carboxyazetidine compound, of the formula

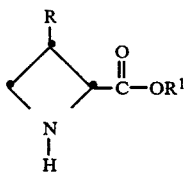

wherein R is alkyl of one to four carbon atoms, $R^1$ is hydrogen or lower alkyl, or a salt thereof.

Preferred esters are the methyl and ethyl esters.

Preferably, R is methyl or ethyl and $R^1$ is hydrogen.

Suitable salts include, for example, the hydrohalide and alkali metal salts of the acid.

The azetidines of Formula I exist in the form of geometric isomers depending on the relative positions of the carboxy and the R groups, and in addition, for each of these geometric isomers, optical isomers exist. As is usual in processes involving biological systems, some isomers may be more active in the process of the invention than other isomers.

The method according to the invention generally produces plants in which male sterility has been induced without an unduly adverse effect upon the female fertility of the plants. The treated plants thus are quite suitable for use in hybrid seed production. Also, the method of the invention can be used in cases where no fruit set is desired—for example, in cases where a plant is to be used for ornamental foliage only, and it is desirable to avoid the mess caused by unwanted fallen fruit.

Although the method of the invention is particularly adapted to treatment of cereal grain plants, it is adapted to treatment of flowering plants, generally. The method thus is of interest with respect to the breeding of such crop plants as wheat, barley, oats, rye, flax, hops, maize, sorghum, buckwheat, millet, triticale, sesame, sunflowers, safflower, soybeans, lentils, mustard, cotton, peanuts, rice, rapeseed, sugarbeets, sugarcane and tobacco; vegetables such as tomatoes, beans, peas, celery and onions; grassy and broadleaved forage crops, such as alfalfa, clover, Sudan grass, lespedeza, vetch and grasses; cucurbits such as cucumbers, squash and melons; crucifers (cole crops) such as cabbage, broccoli and cauliflower; and ornamental plants such as annual and perennial plants of interest in the nursery or home garden trades. The method of the invention also can be used in effecting wide crosses, between different species of plants, where such is possible genetically—as in cross-breeding of different species of cultivated plants, cross-breeding of different species of cultivated and wild plants, and cross-breeding of crop plants with their wild relatives.

It appears that the azetidine has the desired effect when it is applied to the plant at a time during the development of the pollen—i.e., between the time of floral initiation and pollen shed. Preferably, the azetidine is applied somewhat before the pollen is wholly mature, to ensure movement of an effective dosage of the azetidine into the concerned plant tissue, believed to be the pollen grains, in time to effect sterilization of the pollen. For illustration, in the case of small-grain cereal plants, such as wheat and barley, this "application window" appears to extend from about growth stage 32 (second stem node detectable; anthers beginning to differentiate) to about growth stage 49 (awns appearing—i.e., late booting; pollen grains well developed). It appears preferable that the azetidine be applied somewhat earlier than growth stage 47—for example, at about growth stage 43 (boots just visibly swollen—early boot stage). The treatment appears to be most effective when the azetidine is applied after growth stage 32—for example, at about growth stage 37 (flag leaf just visible; early differentiation of ovule and stigma), and before growth stage 47—for example, at about growth stage 39 (flag leaf ligule just visible; meiosis (reduction division) of the pollen mother cells within the anthers). The definitions and meanings of the numbered growth stages are those set out by D. R. Tottman and R. J. Makepeace, Annals of Applied Biology, 93, 221–234 (1979).

The azetidine is suitably applied at a dosage of from 0.05 to 2 kilograms/hectare, preferably 0.05 to 5.0 kilograms/hectare, preferably 0.10 to 2.0 kilograms/hectare.

The present invention also provides a method of producing $F_1$ hybrid seed, which includes cross-pollinating a plant which has been treated by a process according to the invention with a second untreated plant of a different variety or strain.

The azetidine ordinarily will be formulated for use in the method of the invention. The invention, therefore, also provides a pollen-sterilizing composition which comprises a 3-substituted-2-carboxyazetidine, or an alkyl ester, a salt thereof, together with a suitable carrier.

A carrier in a composition according to the invention is any inert material with which the active ingredient is formulated to facilitate application to the plant to be treated, or to facilitate storage, transport or handling. A carrier may be a solid or a liquid, including a material which is normally gaseous but which has been compressed to form a liquid, and any of the carriers normally used in formulating agricultural compositions may be used.

Suitable solid carriers include natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements, for example, carbon and sulfur; natural and synthetic resins, for example, coumarone resins, polyvinyl chloride, and styrene polymers and copolymers.

Suitable liquid carriers include water; alcohols, for example, isopropanol and glycols; ketones, for example, acetone, methyl ethyl ketone, methyl isobutyl ketone and cyclohexanone; ethers; aromatic or araliphatic hydrocarbons, for example, benzene, toluene and xylene; petroleum fractions, for example, kerosene and light mineral oils. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus, preferably, at least one carrier in a composition according to the invention is a surface-active agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulfonic acids; the condensation products of fatty acids or aliphatic amines or amides containing at least 9 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may, for example, be formulated as soluble or wettable powders, solutions, emulsifiable concentrates, emulsions, suspension concentrates and aerosols. Wettable powders usually contain 25, 50 and 75% w of active ingredient and usually contain, in addition to solid inert carrier, 3-10% w of a dispersing agent and, where necessary, 0-10% w of stabilizer(s) and/or other additives such as penetrants or stickers. Emulsifiable concentrates usually contain, in addition to a solvent and, when necessary, co-solvent, 10-50% w/v active ingredient, 2-20% w/v emulsifiers and 0-20% w/v of other additives such as stabilizers, penetrants and corrosion inhibitors.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

In many, if not most, cases, the azetidine is conveniently applied as a water solution containing a small amount of an inert surfactant, a nonionic material being suitable for the purpose. The surfactant of course must be a material that is not toxic to the plant to be treated, at the dosage of the azetidine which is to be used.

The azetidine can be prepared by cyclizing a compound of the general formula

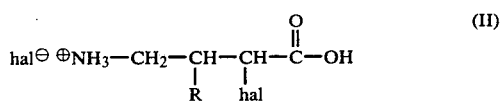

in which each "hal" represents chlorine or bromine, or by cyclizing an ester of a compound of the general formula

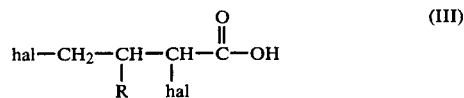

in the presence of an amine, $ANH_2$, wherein A is a moiety that is a protecting group, capable of being removed from the azetidine ring, and subsequently removing the group A from the azetidine ring.

The compound of Formula II may be cyclized by treatment with barium hydroxide, which, if the free acid of Formula II is used, leads to the barium salt of the azetidine 2-carboxylic acid. Preferably, however, the compound of Formula II is prepared by cyclization of an ester of a compound of Formula III in the presence of an amine, which is conveniently carried out by refluxing the two reactants together in a polar solvent, for example, acetonitrile. Preferably, the amine is benzylamine or alpha-phenylbenzylamine, so that the benzyl or alphaphenylbenzyl group can be readily removed from the azetidine ring by hydrogenation under mild conditions by reaction with gaseous hydrogen and a catalyst such as palladium or palladium hydroxide on charcoal.

The compound of Formula II may be prepared using a modification of the Gabriel phthalimide synthesis. A compound of the general formula

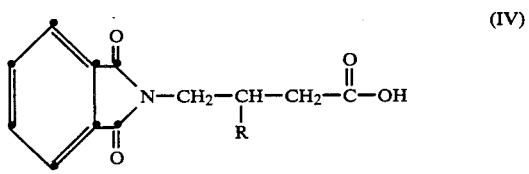

may be halogenated, preferably using bromine and red phosphorus, to produce a compound of the general formula

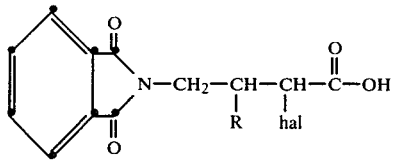

(V)

from which the desired amine hydrohalide can be released by treatment with a hydrohalic acid.

The compound of Formula III may be prepared by reacting a lactone of the general formula

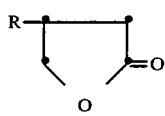

(VI)

with a halogen, preferably bromine, in the presence of red phosphorus, and reacting the product with an alcohol in the presence of an acid catalyst. In a preferred embodiment of the process the alcohol used is benzyl alcohol. It is then possible to react the benzyl ester of the compound of Formula III with benzylamine or alpha-phenylbenzylamine to produce a compound of formula

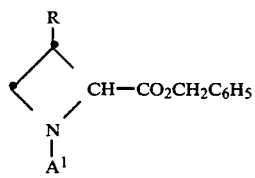

(VII)

where $A^1$ is benzyl or alpha-phenylbenzyl. Subsequent catalytic hydrogenation cleaves both the benzyl ester group and the N-$A^1$ group giving the free acid of Formula I.

The alkyl esters can be prepared by conventional methods—as by treating the acid with thionyl chloride in the presence of the appropriate alkanol. The product is ordinarily the hydrochloride salt, from which the acid can be sprung by known methods. The acids per se appear to be somewhat unstable at ambient temperatures.

The following Examples illustrate the invention. In each case, the identity of each product was confirmed by appropriate chemical and spectral analyses.

EXAMPLE 1

Preparation of 3-methyl-2-carboxyazetidine (1)

(a) 6.5 g of 4-methyltetrahydrofuran-2-one and 0.4 g of red phosphorus were stirred together and heated to 100°-115° C. The mixture was treated with 30 g of bromine until hydrogen bromide began to be evolved. The reaction mixture was then cooled to between 0° and 5° C., 36 g of benzyl alcohol was added, and the mixture was saturated with dry hydrogen chloride. The resulting mixture was allowed to stand for 24 hours. 100 ml of diethyl ether was added, and the mixture was poured into a 3% aqueous solution of sodium bicarbonate, containing ice. The mixture was extracted several times with diethyl ether. The ether extracts were dried over magnesium sulfate, and evaporated. The resulting pale yellow oil was subjected to vacuum distillation: all liquids boiling at a temperature of up to 122° C., 0.6 Torr. were removed. The residue was the benzyl ester of 1,3-dibromo-2-methylbutanoic acid (1A).

(b) 15.0 g of 1A, 27.8 g of alpha-phenylbenzylamine and 250 ml of acetonitrile were refluxed together for 24 hours. The resulting mixture was filtered, evaporated to dryness, triturated with 200 ml of diethyl ether, and filtered again. Dry hydrogen chloride was then passed into the ether solution for 5 minutes. The resulting off-white solid was collected, suspended in 300 ml of chloroform and treated with 20 ml (a slight excess) of triethylamine. The resulting clear solution was evaporated to dryness and extracted with diethyl ether. The resulting ether solution was evaporated, giving 10 g of an oil which was passed over a silica column using as eluent a mixture of ethyl acetate and petroleum ether (boiling point 60°-80° C.) in a ratio 1.5:8.5. Evaporation of the fast-running fractions gave an oil which solidified on standing. The solid was recrystallized from ethanol to give the benzyl ester of 1-diphenylmethyl-2-carboxy-3-methylazetidine (1B), m.p.: 101°-102° C.

(c) 2.0 g of 1B was suspended in 500 ml of ethanol and 20 ml of methanol, 0.5 g of a 5% palladium/charcoal catalyst was added and the mixture was hydrogenated in a Parr apparatus under a hydrogen pressure of between 3 and 4 atmospheres absolute, for 15 hours. The mixture was then filtered and evaporated. Diethyl ether was added, and the aqueous phase was extracted several times and then evaporated to dryness leaving a white solid, which was recrystallized from ethanol to give 1, m.p.: 200°-201° C. with decomposition. NMR showed that the product was a mixture of geometric isomers in the ratio 9:1.

EXAMPLE 2

Preparation of 3-ethyl-2-carboxy azetidine (2)

(a) 21 g of bromine was added to a stirred mixture of 15 g of 4-ethyl-γ-butyro-lactone and 0.3 g of red phosphorus maintained at 120° C. The bromine was added just below the surface of the reactant mixture and during the final stages of bromine addition, the evolution of hydrogen bromide was observed. The reaction mixture was then cooled, 40 ml of benzyl alcohol was added and the resulting solution was saturated with dry hydrogen chloride gas at ambient temperatures. The resulting mixture was allowed to stand for 24 hours. The mixture was then partitioned between ether and a sodium bicarbonate solution and the ether layer was separated and dried over magnesium sulfate. Distillation of the dried solution gave the benzyl ester of 2-bromo-3-bromomethyl pentanoic acid (2A), b.p.: 149° C./0.7 Torr.

(b) 19.5 g of 2A and 29 g of benzhydrylamine in acetonitrile were stirred and refluxed for 48 hours. The resulting mixture was cooled, filtered free of insoluble amine salt and the filtrate evaporated to dryness. The residue, which was a complex mixture of product, was partially purified using a column of silica gel and petroleum ether/ethyl acetate as the eluent. The first fast-running products to emerge were collected and evaporated to dryness, leaving the benzyl ester of 1-diphenyl-methyl-2-carboxy-3-ethylazetidine (2B) as the major component (65% by NMR) of the crude residual mixture.

(c) 8 g of 2B, 100 ml of ethanol and 70 g of 5% palladium charcoal catalyst was hydrogenated at ambient temperature at a hydrogen pressure of between 3 and 4 atomospheres absolute for 10 hours in a Parr apparatus. The resulting mixture was filtered, evaporated to dryness and partitioned between methylene chloride and water. The aqueous phase was separated, evaporated to a low bulk and poured onto a Dowex 8-50 x(H) resin column. Isolation of the imino acid was achieved by eluting the washed column with a 2M ammonia solution. Evaporation of the washings left a white solid which on recrystallization from ethanol deposited an isomer mixture [1α:3β] of 2. Evaporation of the recrystallizing medium left additional 2, having a different isomer composition [2α:3β].

EXAMPLE 3

Preparation of cis-3-methyl-2-carboxyazetidine 3 and trans-3-methyl-2-carboxyazetidine (4)

A stirred mixture of 36.06 g of crotyl alcohol, 162.2 g of triethyl orthoacetate and 2.22 g of propionic acid was slowly heated to 100° C. (1.25 hours), stirred and heated at 100°–115° C. for 1 hour, at 115°–145° C. for 2.5 hours, then at 145°–155° C. for 6 hours. The mixture was cooled in an ice bath and treated with 50 ml of glacial acetic acid and 50 ml of water. The mixture was stirred at room temperature for 45 minutes, diluted with ether, extracted with saturated sodium bicarbonate solution, then with brine and dried ($MgSO_4$). The solvent was evaporated under reduced pressure and the residue was distilled under reduced pressure to give ethyl 3-methyl-4-pentenoate (3A), as a colorless liquid, b.p.: 88°–91° C. (60 Torr.).

A solution of 53.18 g of 3A in 400 ml of dry methylene chloride was cooled to −78° C. Ozone was passed through the cold solution for 3.5 hours, air was passed through the solution for 10 minutes, then the solution was allowed to warm. At −50° C., 41.63 g of triethylamine was added drop-by-drop slowly. A strongly exothermic reaction occurred immediately, and the mixture was maintained at 5°–10° C. over the period of addition of the amine (30 minutes). The mixture then was stirred at room temperature for 2 hours, the solvents were evaporated under reduced pressure, and the residue was vacuum-chromatographed on silica gel, ether being used as eluent. The solution thus obtained was dried ($MgSO_4$) and the solvent was evaporated to give ethyl 3-methyl-4-oxobutanoate (3B), as a slightly unstable pale yellow oil.

2.74 g of sodium borohydride was added in portions over 30 minutes to a stirred solution of 38.91 g of 3B in 400 ml of ethanol at 0°–10° C. The mixture was stirred at room temperature for 2 hours, 25 ml of water was added and the mixture was stirred at room temperature for 10 minutes. The solvents were evaporated under reduced pressure, the residue was triturated and stirred with 500 ml of ethyl acetate, and dried ($MgSO_4$). The solvent was evaporated and 0.65 g of p-toluenesulfonic acid was added and the mixture was distilled slowly over 2 hours in a Kugelrohr apparatus to give a liquid, b.p.: 85°–105° C. (14 Torr.), which was mixed with 0.50 g of p-toluenesulfonic acid and distilled to give beta-methyl-gamma-butyrolactone (3C), as a clear liquid, b.p.: 85°–95° C. (14 Torr.).

A mixture of 15.0 g of 3C and 0.93 g of red phosphorus was stirred and heated to 105° C. Then 50.0 g of bromine was added drop-by-drop beneath the surface of the stirred mixture. During the addition, two additional portions of 0.47 g of red phosphorus were added. The two reagents were added at rates such as to maintain the temperature of the mixture at 110°–115° C. The additions took place over about 1.5 hours. The mixture was cooled to room temperature, excess bromine was removed by sparging the mixture with nitrogen, the mixture was cooled to 0° C. and 81.1 g of benzyl alcohol was added, with stirring, at a rate such as to maintain the mixture temperature at about room temperature. The resulting solution was saturated with dry hydrogen chloride and stirred at 0° C., then at room temperature overnight (17 hours). The mixture was diluted with 600 ml of ether and extracted, successively, with 10% aqueous sodium hydroxide solution, saturated sodium bicarbonate solution, water and brine, and dried ($MgSO_4$). The solvent was evaporated and the residue was distilled to give benzyl 2,4-dibromo-3-methylbutyrate (3D), as a colorless liquid, b.p.: 136°–141° C. (0.6 Torr.).

A stirred mixture of 23.94 g of 3D, 37.6 g of aminodiphenylmethane and 170 ml of acetonitrile was refluxed for 40 hours. The mixture was cooled, filtered and the filtrate was concentrated to dryness under reduced pressure. The residue was dissolved in the minimum amount of methylene chloride, the solution was filtered through a short column of silica gel, using a 2:1 v:v mixture of hexane and ether as eluent. The solvents were evaporated. The residue was subjected to high pressure liquid chromatography (HPLC) twice, using an 8:1 v:v mixture of hexane and ether as eluent. The less polar portions thus obtained were combined, the solvents were evaporated and the residue crystallized from methylene chloride/hexane to give N-diphenylmethyl-cis-3-methyl-2-azetidinecarboxylic acid benzyl ester (3E), as a colorless solid, 112°–113.5° C.

The more polar portions that were obtained were combined, the solvents were evaporated, the residue was re-purified by HPLC, using a 9:1 v:v mixture of hexane and ether as eluent to give the trans isomer (3F), as a viscous oil.

A suspension of 8.80 g of 3E and 2.20 g of 5% palladium-on-charcoal catalyst in 250 ml of ethanol was hydrogenated (50 psig) in a Parr shaker for 15 hours. The mixture then was filtered through a pad of Celite containing anhydrous magnesium sulfate, the solvent was evaporated from the filtrate under reduced pressure, the residue was dissolved in 100 ml of water and extracted with ether. The water was evaporated from the aqueous phase and the residue was recrystallized from water and ethanol to give impure 3. The mother liquor was diluted with ethanol to give 3, as a colorless solid, m.p.: 204°–205° C. (with decomposition). The impure 3 and the residue from the mother liquor were combined, dissolved in the miniumum amount of water and applied to a column of Dowex 50X8200 cation exchange resin. The column was eluted with 300 ml of 0.1N hydrochloric acid, then with 2N aqueous ammonia. Evaporation of solvent and recrystallization of the residue from ethanol gave further 3, as a colorless solid, m.p.: 202°–204° C.

8.94 g of 3F was hydrogenated in the same way. Following filtration of the reaction mixture, the solvent was evaporated from the filtrate under reduced pressure, the residue was dissolved in 100 ml of water, extracted with ether, and the water was evaporated from the aqueous phase under reduced pressure, followed by drying under high vacuum gave a colorless solid, which on recrystallization from ethanol gave 4, m.p.: 184.5°–186.0° C. (with decomposition).

EXAMPLE 4

Demonstration of pollen-sterilizing activity

Spring wheat, variety Sicco, was propagated in a glasshouse in 13 centimeter pots containing a loam-based compost. Supplementary lighting was provided by high-pressure mercury vapor lamps to give a constant day length of 16 hours. The temperature was maintained at approximately 20° C.

The compound to be tested was formulated as an aqueous solution containing 0.1% Nonidet P 40 (trade mark) as wetting agent and 1% acetone to aid solubility. This formulation was dilted with water to a concentration of 1000 parts per million, and sprayed onto plants to runoff. The plants were treated at the growth stage when the second node of the plant was just detectable.

At ear emergence but before anthesis, 5 heads from each treated pot were placed in cellophane bags to prevent cross-pollination. At maturity, the bagged ears were harvested, and seed set was recorded and compared with untreated controls.

The results are shown in the following table.

| Compound No. | Grain Set Inhibition (% of control) |
|---|---|
| 1 | 69 |
| 2 | 68 |

It can be seen that the test compounds produced a considerable reduction in seed set compared with the untreated control, clearly illustrating the ability of the compounds to sterilize the male parts of the wheat.

EXAMPLE 5

The capability of wheat plants to set seed by cross-pollination, following treatment of the plants with Compounds 3 and 4, was assessed as follows:

Plants of spring wheat (*Triticum aestivum* cv. Yecora rojo) were grown in pots in a greenhouse under controlled conditions. The test compound was applied as an aqueous solution containing 0.75% Tween 20 as surfactant, at the rate of 600 liters per hectare. Control plants were sprayed with water containing 0.75% Tween 20. The test compound was applied at dosages of 1000 to 2000 grams per hectare, and was applied to the plants during spike development prior to head emergence. The stage of development (length of spike primordia) was determined by measuring the lengths of a random sample of five spikes. All were in the range of 1.5 to 4.0 centimeters in length (stages 32–43, Zadok's scale).

Following treatment, the plants were placed in a randomized block arrangement, with at least four replicates per treatment.

As the spikes emerged, the mainstem and first tiller of each plant were bagged to prevent cross-pollination. In some cases, half of the mainstem spikes per pot were hand-crossed with pollen from untreated plants. Control spikes were hand-crossed, but not emasculated.

When the developing seeds reached the soft dough stage, water was withheld, to dry the seeds for harvest, and the number of seeds that had been set were counted. The following results were obtained.

TABLE 1

| Compound | (g/ha) | Timing[a] | Seed set, treated heads[b] Mainstem | Seed set, treated heads[b] Tiller | Seed Set, hand-crossed heads[b] |
|---|---|---|---|---|---|
| 3 | 1000 | 1.5 | 2.8 ± 7.5 | 5.3 ± 2.8 | 19.1 ± 3.0 |
|   | 2000 | 1.5 | 0 | 0.3 ± 0.2 | 13.5 ± 3.5 |
| 4 | 1000 | 1.5 | 9.9 ± 1.1 | 8.2 ± 1.3 | 22.5 ± 3.4 |
|   | 2000 | 1.5 | 0.5 ± 0.4 | 2.8 ± 2.6 | 13.5 ± 3.5 |
| Control | — | — | 31.9 ± 3.4 | 18.9 ± 2.2 | 29.1 ± 1.1 |
| 3 | 1000 | 4.0 | 20.3 ± 3.7 | 16.9 ± 2.0 | 27.3 ± 1.3 |
|   | 2000 | 4.0 | 10.6 ± 5.1 | 4.9 ± 1.4 | 17.4 ± 6.2 |
| 4 | 1000 | 4.0 | 23.4 ± 4.8 | 16.0 ± 2.6 | 26.1 ± 3.1 |
|   | 2000 | 4.0 | 20.4 ± 4.5 | 12.2 ± 4.0 | 28.4 ± 2.5 |
| Control | — | — | 26.6 ± 1.8 | 17.8 ± 1.1 | 25.5 ± 0.7 |

[a]Spike primordium length, cm.
[b]Average seed set per bagged head ± standard error.

I claim:

1. A method for producing male sterility in a cereal grain plant without substantial effect on the female fertility of the plant, which comprises applying to the plant an effective dosage of an azetidine of the formula

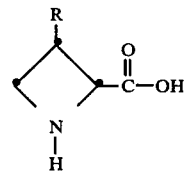

wherein R is alkyl of one to four carbon atoms, or a salt thereof.

2. A method according to claim 1 wherein R is methyl.

3. A method according to claim 1 wherein R is ethyl.

4. A method for producing a hybrid seed which comprises applying to a candidate parent cereal grain plant a male sterilizing effective dosage of an azetidine of the formula

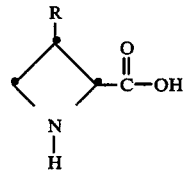

wherein R is alkyl of one to four carbon atoms, or a salt thereof, thereafter causing the candidate plant to be pollinated with pollen from a candidate male parent plant, allowing the pollinated parent to mature until the seed is mature, and harvesting the seed.

5. A method according to claim 4 wherein R is methyl.

6. A method according to claim 4 wherein R is ethyl.

7. A method according to claim 1 wherein the azetidine is a hydrohalide or alkali metal salt of the azetidine of the said formula.

* * * * *